United States Patent [19]

Komiyama et al.

[11] Patent Number: 5,639,425

[45] Date of Patent: Jun. 17, 1997

[54] ANALYZING APPARATUS HAVING PIPETTING DEVICE

[75] Inventors: Yasuaki Komiyama; Ryuji Tao; Hiroyasu Uchida, all of Hitachinaka, Japan

[73] Assignee: Hitachi, Ltd., Tokyo, Japan

[21] Appl. No.: 529,802

[22] Filed: Sep. 18, 1995

[30] Foreign Application Priority Data

Sep. 21, 1994 [JP] Japan .................................. 6-226226

[51] Int. Cl.⁶ .................................................. G01N 35/10
[52] U.S. Cl. .................... 422/63; 422/64; 422/65; 422/100; 422/104; 436/43; 436/47; 436/48; 436/49; 436/54; 436/180; 73/864.24; 73/864.25
[58] Field of Search .......................... 422/63, 64, 65, 422/67, 68.1, 99, 100, 104; 436/43, 47, 48, 49, 180, 183, 54; 73/864.01, 864.24, 864.25, 864.31

[56] References Cited

U.S. PATENT DOCUMENTS

| | | | |
|---|---|---|---|
| 4,087,248 | 5/1978 | Miles . | |
| 4,287,155 | 9/1981 | Tersteeg et al. | 422/64 |
| 4,456,037 | 6/1984 | Gocho | 141/1 |
| 4,824,641 | 4/1989 | Williams | 422/100 |
| 4,906,433 | 3/1990 | Minekane | 422/64 |
| 4,927,545 | 5/1990 | Roginski | 210/745 |
| 5,008,082 | 4/1991 | Shaw | 422/65 |
| 5,013,529 | 5/1991 | Itoh | 422/100 |
| 5,104,621 | 4/1992 | Pfost et al. | 422/67 |
| 5,164,318 | 11/1992 | Sato et al. | 435/288 |
| 5,190,727 | 3/1993 | Hirsch | 422/67 |
| 5,200,151 | 4/1993 | Long | 422/100 |
| 5,213,764 | 5/1993 | Kerr et al. | 422/100 |
| 5,422,075 | 6/1995 | Saito et al. | 422/52 |
| 5,472,669 | 12/1995 | Miki et al. | 422/63 |

FOREIGN PATENT DOCUMENTS

| | | |
|---|---|---|
| 282076A2 | 9/1988 | European Pat. Off. . |
| 557828A1 | 9/1993 | European Pat. Off. . |
| 3733098A1 | 4/1988 | Germany . |
| 4306332A1 | 8/1994 | Germany . |
| 59-188538 | 10/1984 | Japan . |
| 4-296655 | 10/1992 | Japan . |
| 6-88828 | 3/1994 | Japan . |
| 6-27743 | 4/1994 | Japan . |

*Primary Examiner*—Long V. Le
*Attorney, Agent, or Firm*—Fay, Sharpe, Beall, Fagan, Minnich & McKee

[57] ABSTRACT

An analyzing apparatus has a transfer device having a movable gripper, a pipetting device having a movable nozzle and a measuring unit. One of a plurality of tips arranged on a tip rack and one of a plurality of vessels arranged on a vessel rack are held by the gripper to be set in a tip holder. A nozzle pushes the tip on the tip holder to connect to the tip. A sample and reagents are delivered into a vessel on the tip holder by the tip connected to the nozzle. The used tip is detached from the nozzle. The vessel containing a reaction mixture is transferred to a sucking position with the gripper after incubation, and the reaction mixture is introduced into the measuring unit. The used vessel is transferred to a waste box with the gripper.

13 Claims, 3 Drawing Sheets

FIG. 3

ANALYZING APPARATUS HAVING PIPETTING DEVICE

BACKGROUND OF THE INVENTION

The present invention relates to an apparatus for analyzing a liquid sample such as a biological sample, and more particularly to an analyzing apparatus having a pipetting device for transferring a sample from a sample cup to a reaction vessel.

In an automated analyzing apparatus for analyzing many kinds of analytical items by reacting a biological sample with reagents, an analyzing apparatus is widely employed of a type in which a row of reaction vessels are transferred with a turntable, as disclosed in, for example, Japanese Patent Publication No.6-27743 (1994) and Japanese Patent Application Laid-Open No.6-88828 (1994).

Japanese Patent Application Laid-Open No.6-88828 (1994) teaches an immunoassay apparatus which comprises a reagent unit having a turntable arranging reagent bottles, a sample transfer unit for transferring a sample rack to a sample pipetting position on the transfer path, a reagent delivery unit for delivering reagents from the reagent unit to a reaction table, and a sample delivery unit for deliver a sample from the sample rack to the reaction table.

On the other hand, a sample delivery apparatus without turntable is disclosed in Japanese Patent Application Laid-Open No.4-296655 (1992). In this conventional technology, test tubes which are empty, sample cups and nozzle tips are arranged on an X-Y stage, and the disposable nozzle tip is connected to a nozzle communicated with a pump, to deliver the sample cup to the test tube.

The inventors of the present invention have tried to realize an automated analyzing apparatus using disposable nozzle tips and disposable reaction vessels. However, when the method of delivering a tip as in Japanese Patent Application Laid-Open No.4-296655 (1992) is employed in this analyzing apparatus, it is necessary to connect the tip to the nozzle on the tip array region on the X-Y stage.

In this case, since a pushing force is applied against the tip rack when the tip is connected to the nozzle, the tip rack needs to have a strong structure. If an operator of the analyzing apparatus reuses the tip rack, many tips on the tip rack must be arranged by hand. On the other hand, if a tip rack having a strong structure is used, extra cost is required.

SUMMARY OF THE INVENTION

An object of the present invention is to provide an analyzing apparatus capable of properly connecting a tip to a nozzle of a delivery device without forming a tip rack for arranging many nozzle tips in a strong structure.

Another object of the present invention is to provide an analyzing apparatus capable of decreasing the number of consumed disposable tips by using one disposable tip and delivering one sample and a plurality of reagents.

An analyzing apparatus according to the present invention comprises a tip rack for arranging a plurality of nozzle tips, a pipetting device for transferring a liquid sample from a sample cup to a reaction vessel using a disposable nozzle tip connected to a nozzle movable in a first predetermined region, a tip holder provided in the first predetermined region, a tip gripper movable in a second predetermined region, and a transfer device for transferring a nozzle tip on the tip rack to the tip holder using the tip gripper.

The disposable tip transferred by the tip gripper is connected to the nozzle of the pipetting device by pushing the nozzle tip to the nozzle on the tip holder. Therefore, the tip holder is made of a material having a stiffness that is large enough to endure the pushing force of the nozzle. However, since the tip rack having a lot of arranged nozzle tips does not receive the pushing force, the tip rack is made of a material of low strength which is capable of supporting the tips. In this case, the tip rack is preferably a thin molded plastic. The tip rack has many tip insertion holes arranged at given intervals in the X-direction and Y-direction so that positions of a large number of tips are accurately determined. The tip racks are supplied from a vendor with the tips inserted. Thus, there is no need for a user to set the many tips on the tip rack.

In a preferred embodiment, the tip holder comprises a tip connecting station, a sample receiving station and a tip detaching station. The nozzle tip connected to the nozzle at the tip connecting station is cleaned with the cleaning unit after a reagent is transferred to the reaction vessel. After cleaning, the nozzle tip transfers a sample to the reaction vessel, and then is detached from the nozzle at the tip detaching station.

BRIEF DESCRIPTION OF THE DRAWINGS

FIG. 3 is a schematic view explaining the operation of the analyzing apparatus of FIG. 1.

DETAILED DESCRIPTION OF THE PREFERRED EMBODIMENTS

An embodiment according to the present invention will be described below, referring to FIG. 1 to FIG. 4.

Figure 1:
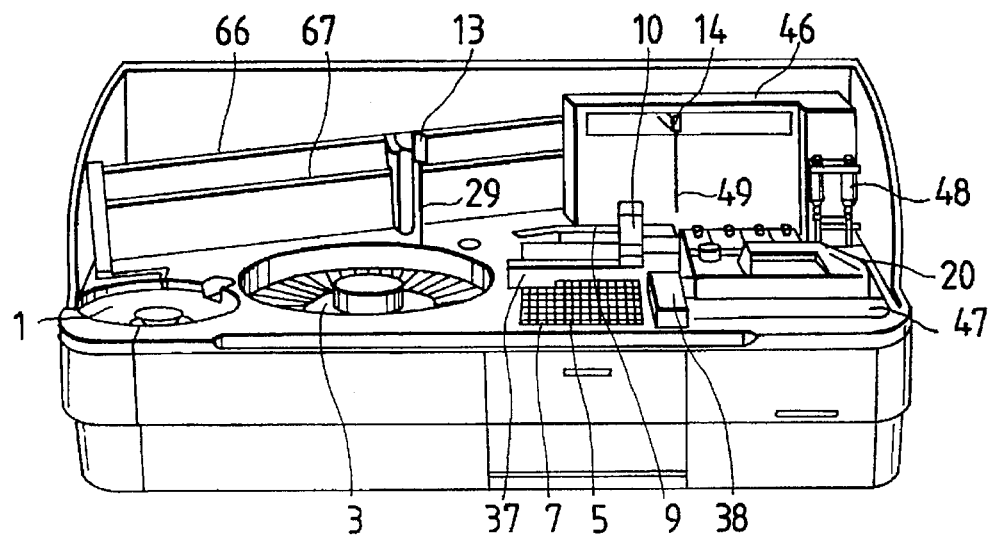
FIG. 1 is a view showing the outward appearance of one embodiment of an analyzing apparatus in accordance with the present invention.

In FIG. 1, a sample supplying device has a turntable 1 on which many sample cups are arranged. A reagent positioning device has a turntable 3 on which reagent bottles corresponding to plural analytical items are arranged. In a rack supplying area, three tip racks 5 and three vessel racks 7 are placed. A transfer device has a fixed rail 38, a rail 37 movable on the rail 38, and a movable gripper 10 moving on the rail 37.

A pipetting device has a movable member 13 and a pipetting nozzle 29 supported by the movable member 13. An incubator unit 9 heats a plurality of reaction vessels containing mixtures of a sample and a reagent at a certain temperature, for example 37° C. A measuring unit 46 has a flow cell and an optical system for measuring a reaction liquid in the flow cell. A tube 49 for sucking the reaction liquid is suspended from a movable arm 14. A reaction liquid sucked by the sucking operation of a syringe mechanism 48 through the tube 49 is introduced into the flow cell of the measuring unit 46 to be measured. After measurement, the reaction liquid is collected in a waste tank 20. A control unit 47 controls the operation of each mechanism in the analyzing apparatus.

Figure 2:
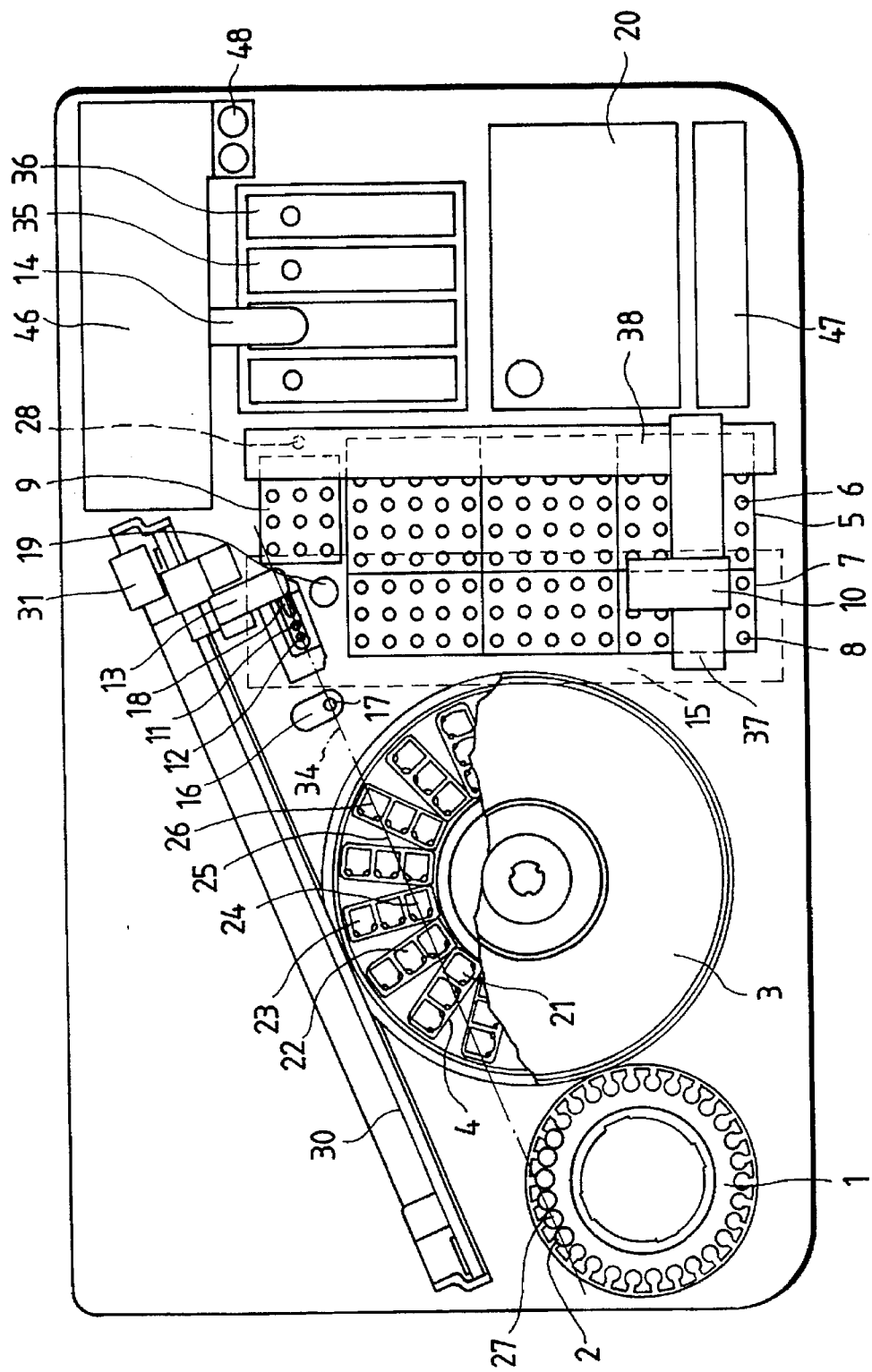
FIG. 2 is a schematic plan view of the analyzing apparatus of FIG. 1.

In FIG. 2, on the turntable I there are arranged many sample cups 2 containing biological samples such as blood or urine. The turntable I is intermittently rotated to position each of the sample cups 2 at a sucking position 27. On the turntable 3 there are arranged many reagent bottles 4. The reagent bottle 4 has three rooms 21, 22, 23. The reagent bottle 4 is placed so that a first reagent room 21 comes in the inner peripheral side. Therefore, when all the reagent bottles are set, three concentric circles are formed around the center of the rotation. That is, a ring, or row, of the first reagent rooms 21 is formed along an innermost concentric circle, a ring or row, of the second reagent rooms 22 is formed along an intermediate concentric circle, and a ring, or row, of the third reagent rooms 23 is formed along an outermost concentric circle. As the turntable 3 is intermittently rotated, the first reagent room 21 is positioned at a sucking position 24, the second reagent room 22 is positioned at a sucking position 25, and the third reagent room 23 is positioned at a sucking position 26.

Figure 4:
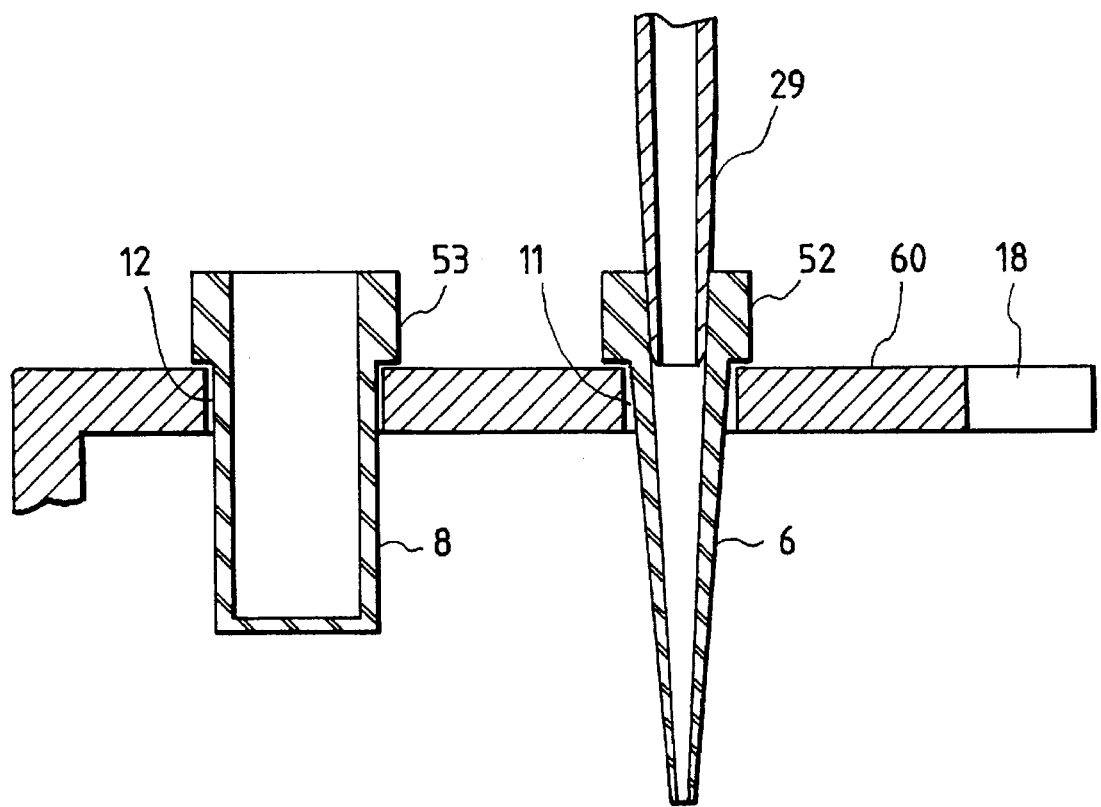
FIG. 4 is a view explaining the state of connecting a tip to a nozzle in a pipetting device.

Three tip racks 5 are mounted on a rack supplying area in the moving region of the gripper 10. Beside the three tip racks 5, three vessel racks 7 are mounted. In each of the tip racks 5, tip insertion holes spaced at equal intervals are formed in the X-direction and in the Y direction to accommodate nozzle tips 6. Each nozzle tip 6 has a nearly conical thin tube with a jaw 52 held by the gripper 10 as shown in FIG. 4.

The nozzle tip 6 is formed of a resin such as polypropylene. The tip rack 5 is a thin molded plastic and has legs 51. The tip rack 5 is formed of a resin such as polypropylene. Many unused nozzle tips 6 are mounted on the tip rack 5.

The structure of the vessel rack 7 is the same as that of the tip rack 5. The reaction vessel 8 is a molded plastic with a jaw 53 as shown in FIG. 4. The jaw 53 is grasped by the gripper 10.

The incubator 9 in FIG. 2 has a thermal-conductive metal member and a heating unit for heating the metal member at a given temperature. In the metal member, there are formed a plurality of holes into which the reaction vessels are inserted. These holes are open upward.

Figure 3:
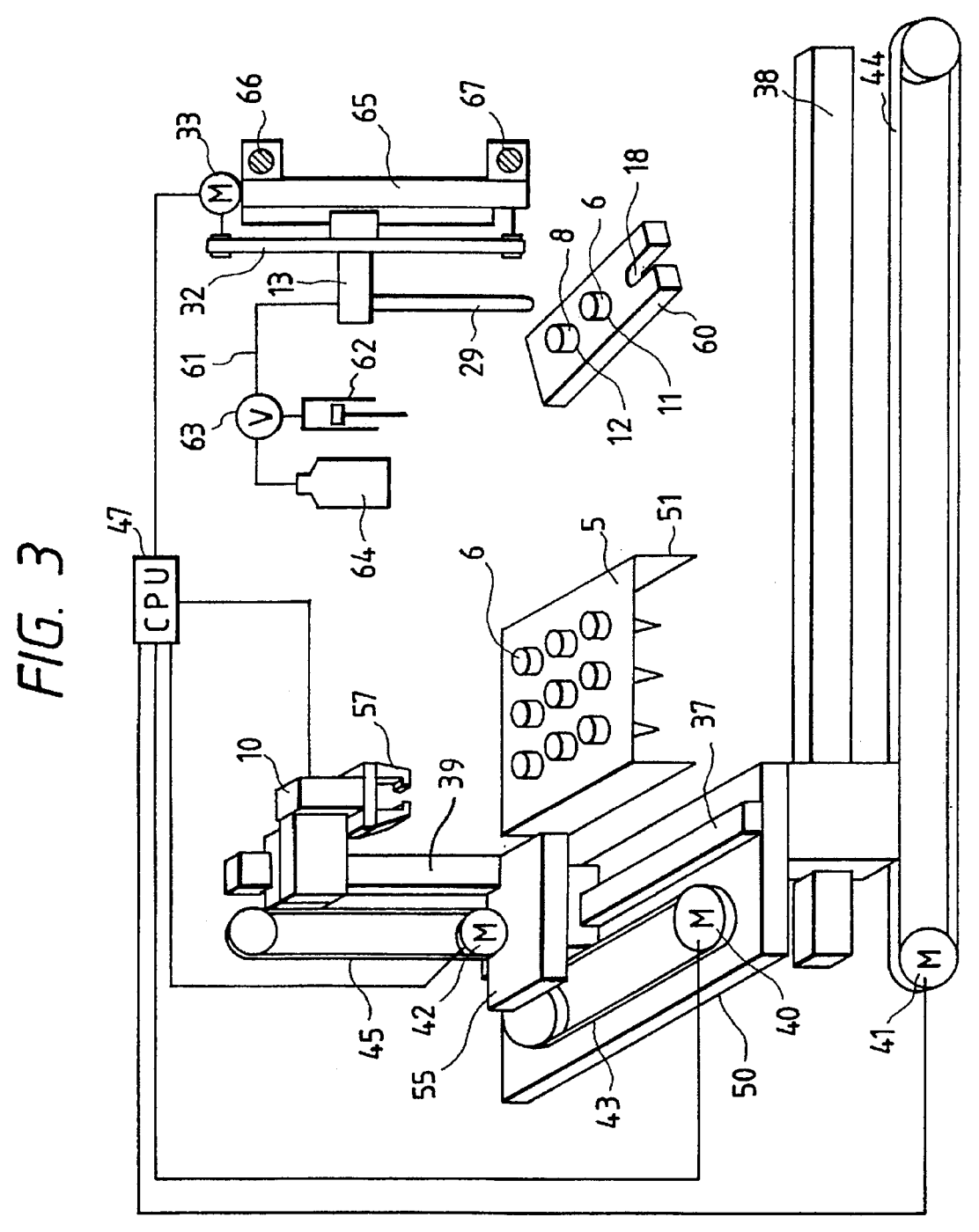

In FIG. 2 and FIG. 3, a transfer device for selectively transferring the nozzle tip and the reaction vessel has the rail 38 extending in the Y-direction. A base 50 having the rail 37 extending in the X-direction is connected to a belt 44 and moved on the rail 38 in one direction or the opposite direction with the belt 44 rotated by a motor 41 controlled by the control unit 47.

The base 50 has a motor 40 for rotating a belt 43. A base 55 is slidably attached to the rail 37 on the base 50. The base 55 is connected to the belt 43 and moved on the 5 rail 37 in the longitudinal direction of the rail 37 by rotation of the motor 40. The base 55 has a motor 42 for rotating a belt 45 and a vertical rail 39.

The movable gripper 10 is slidably attached to the vertical rail 39, and moved upward and downward according to motion of the belt 45. The movable gripper 10 has a pair of reclosable claws 57 capable of gripping either the nozzle tip 6 or the reaction vessel 8. The operation of releasing and gripping of the pair of claws 57 is controlled by the control unit 47.

The movable gripper 10 grips each unused tip 6 on the tip rack 5 one-by-one using the claws 57 to transfer it to a tip holder 60, and releases the tip 6 after inserting the tip 6 into a hole of the tip connecting station 11 in the holder 60. Further, the movable gripper 10 grips each unused vessel 8 on the vessel rack 7 one-by-one using the claws 57 to transfer it to a tip holder 60, and releases the vessel 8 after inserting the vessel 8 into a hole of the sample receiving station 12 in the holder 60. These operations are repeated at intervals of a given period.

As shown in FIG. 2, FIG. 2 and FIG. 4, the sample receiving station 12, the tip connecting station 11 and the tip detaching station 18 on the tip holder 60 are linearly arranged along the horizontal moving locus 34 of the nozzle 29 of the pipetting device. The tip cleaning position 17, the reagent sucking positions 24, 25, 26 and the sample sucking position 27 are arranged along the horizontal moving locus 34 of the nozzle 29. The locus 34 passes through an area off the rotating center of the turntable for reagents and linearly passes across the three concentric circles. The tip holder 60 receiving the tip 6 and the vessel 8 from the movable gripper 10 is installed in an area overlapped with the movable region of the movable gripper 10 and the movable region of the nozzle 29 of the movable member 13.

The movable member 13 of the pipetting device is, as shown in FIG. 3, connected to a belt 32 rotated between a pair of pulleys driven by a motor 33 to travel upward and downward according to motion of the belt. The nozzle 29 supported to the movable member 13 is connected to a syringe pump 62 through a conduit 61. The pump 62 is connected to a cleaning tank 64 through a switching valve 63. A slider 65 having the movable member 13 and the motor 33 is horizontally moved along a pair of rails 66, 67. As shown in FIG. 2, the slider 65 is connected to a belt 30 and horizontally moved by rotation of the belt 30 driven by a motor 31.

After the disposable tip 6 is put in the tip holder 60 by the movable gripper 10, the motor 33 is started to drive based on a command of the control unit 47 to move the movable member 13 downward. As shown in FIG. 4, the end of the nozzle 29 moved down is inserted into the tip 6. By pushing the nozzle down further, the outer wall of the nozzle 29 is tightly connected to the inner wall of the tip 6. Therefore, the pushing force from the nozzle 29 is applied to the tip holder 60. The tip holder 60 is made of a material that can withstand such a pushing force, for example, stainless steel plate of 8 mm thickness.

When the nozzle 29 is moved upward as the motor 33 drives, the tip 6 connected to the nozzle 29 is also moved upward together with the nozzle. After the tip delivers the reagents from the reagent bottles 24, 25 and 26 and the sample from the sample cup 2 to the reaction vessel 8, the tip was finished its role, and is transferred to the tip detaching station 18 of the tip holder 60. The tip 6 is moved downward and in the lateral direction so that the upper portion of the jaw 52 of the tip 6 touches the lower portion of the station 18 by motion of the nozzle 29. Then the nozzle 29 is moved upward to hook the upper portion of the tip to the tip holder 60 and the tip 6 is detached from the nozzle 29.

A box 15 for receiving waste having a size extending over the vessel rack supplying area and the tip holder 60 is placed below. A collecting bag made of vinyl chloride is set inside the box 15. The used tip 6 detached at the 5 tip detaching station 18 is dropped and collected in the bag. There is a vessel throwing-out hole 19 opened on the top of the box 15. The used reaction vessel 8, after the reaction liquid has been sucked at the reaction liquid sucking position 28, is gripped by the movable gripper 10 and transferred from the sucking position 28 to the throwing-out hole 19. Then the gripper 10 is released over the hole 19 to drop the used vessel 8 into the box 15. In order to collect the waste, all that an operator has to do is to exchange the bags. Therefore, the operator touches neither the used tips 6 nor the used vessels 8.

The sucking tube 49 supported by the movable arm 14 is moved both horizontally and vertically. The tube 49 is lowered into the reaction vessel 8 placed at the sucking position 28, and the reaction liquid is conducted to the flow cell of the measuring unit 46 by operation of the syringe mechanism 48. Then the tube 49 is moved upward and transferred to a cleaning solution bottle 36. After the tube 49 is moved down and the cleaning solution is conducted to the flow cell through the tube 49, the tube 49 is moved upward and transferred to a buffer solution bottle 35. The tube 49 is moved downward and a buffer solution is conducted to the flow cell through the tube 49. Then the tube 49 is moved upward and transferred to the sucking position 28 for the next reaction liquid. The various kinds of solutions passing through the measuring unit 46 are collected into the waste liquid tank 20.

Operation of an automated analyzing apparatus will be described below.

The nozzle tips 6 are supplied by a vendor in a state of being arranged in the tip rack 5. The unused reaction vessels 8 are also supplied by a vendor in a state of being arranged in the vessel rack 7. An operator mounts such a tip rack 5 and such a vessel rack 7 on the tip supplying area. The sample cups 2 containing samples to be analyzed are arranged on the turntable 1, and reagent bottles 4 corresponding to analytical items are arranged on the turntable 3.

The movable gripper 10 is moved onto the tip rack 5 and moved down with the claws 57 kept open to grip one of nozzle tips 6 at the jaw 52 by closing the claws 57. The gripper 10 is moved upward in this state and then horizontally moved to transfer the nozzle tip 6 to the tip holder 60. The tip 6 is placed at the tip connecting station 11 by the gripper 10 and released from the gripper 10 by opening the claws 57. The nozzle 29 is moved down to the tip connection station 11, and the nozzle 29 is connected to the tip 6 by pushing the nozzle 29 in the tip 6.

Then the nozzle 29 is moved upward and the tip 6 connected to the nozzle 29 is horizontally moved toward the sucking position 24 on the turntable 3. During that time, the movable gripper 10 is moved onto the vessel rack 7 and grips one of the vessels 8 at the jaw 53 of the vessel 8 to place it to the sample receiving station 12 of the tip holder 60.

A given amount of the first reagent is sucked into the tip 6 by the pump 62, and the tip 6 is moved down into the first reagent room 21 positioned at the sucking position 24. The tip 6 having the first reagent is moved upward and horizontally moved to the sample receiving station 12. The reagent then delivered from the tip 6 into the vessel 8. Then the tip 6 is moved upward and transferred to the cleaning tank 17. The cleaning tank 17 is supplied with cleaning solution from the cleaning unit 16. The tip 6 is the cleaned in the cleaning tank 17.

During cleaning of the tip 6, the turntable 3 is rotated to position the second reagent room 22 on the intermediate concentric circle at the sucking position 25. The cleaned tip 6 is inserted into the second reagent room 22 of the sucking position 25 to suck a given amount of the second reagent. The upwardly moved tip 6 is transferred to the sample receiving station 12 to deliver the second reagent into the vessel 8. Then, the tip 6 is cleaned in the cleaning tank 17. The turntable 3 moves the third reagent room 23 in the outermost circle to the sucking position 26. The third reagent sucked in the tip 6 is delivered into the vessel 8 on the station 12. The nozzle tip 6 having delivered the reagent is again cleaned in the cleaning tank 17. The cleaned tip 6 is moved to the sucking position 27 of the turntable 1, and moved down into the sample cup 2 positioned at position 27. A given amount of the sample is sucked into the tip 6 by operation of the pump 62. The tip 6 is upward and horizontally moved, and moved downward at the sample receiving station 12 of the tip holder 60 to deliver the sample in the tip 6 into the reaction vessel 8 already containing the reagents.

After finishing delivery of the reagent and the sample, the tip 6 is transferred to the detaching station 18 to be detached from the nozzle 29. The reaction vessel 8 containing the mixture of the sample and reagent is gripped by the movable gripper 10 at the jaw 53 to be inserted into a vacant receiving hole in the incubator 9 and released from the gripper 10. The vessel 8 is incubated at a constant temperature for a given time period determined depending on the analytical item. In the incubator 9, reactions of plural samples proceed in parallel. After the given reaction time has passed, the reaction vessel 8 is lifted by the gripper 10 to be set in the sucking position 28. The reaction liquid sucked from the tube 49 is conducted to the flow cell of the measuring unit 46. The vacant vessel 8 is gripped by the gripper 10 at the sucking position 28 and transferred to the throwing-out hole 19 to be thrown out.

During the time when the vessel 8 is staying at the incubator 9, the transfer device transfers a disposable tip 6 and a vessel 8 for the next sample to the tip holder 60, and the pipetting device performs a pipetting operation of the reagent and the sample. By repeatedly supplying tips 6 and vessels 8 using the movable gripper 10, all the tips 6 on the rack 5 and all the vessels 8 on the rack 7 will be used, upon which the analyzing apparatus completes the analyzing operation.

According to the aforementioned embodiment, since the apparatus is constructed so that the tip 6 is connected to the nozzle 29 at the tip holder 60 and only the work to lift and draw out the tip 6 using the movable gripper 10 is performed at the tip rack, no excessive force is applied to the tip rack. Therefore, the tip rack can be formed of a material that is as comparatively low in strength, requiring only that the tip rack support many tips spaced from one another. Since such a tip rack is supplied by a vendor in a state where many tips are orderly arranged, it is unnecessary for an operator to arrange the tips in the tip rack.

Since work done by the transfer device and work done by the pipetting device can be performed in parallel, a high analyzing efficiency can be attained. Since a sample and reagents are pipetted using a single disposable tip, the number of consumed tips can be decreased. Since both of the tip connecting station and the sample receiving station are installed in a place where the movable region of the gripper 10 and the movable region of the nozzle 29 are overlapped, the analyzing apparatus can be made small.

What is claimed is:

1. An analyzing apparatus, comprising:

a pipetting device for transferring a liquid sample from a sample cup to a reaction vessel using a disposable nozzle tip connected to a nozzle, said nozzle being movable in a first given region:

a tip rack on which a plurality of nozzle tips are arranged;

a tip holder provided in said first given region;

a gripper movable in a second given region; and a transfer device for removing said nozzle tips one-by-one from said tip rack and transferring the nozzle tips individually to said tip holder using said gripper;

wherein said pipetting device connects said nozzle to a nozzle tip held on said tip holder by pushing said nozzle against said nozzle tip.

2. An analyzing apparatus according to claim 1, wherein said tip holder is made of a material having a stiffness that withstands a pushing force of said nozzle when said nozzle is pushed against said nozzle tips.

3. An analyzing apparatus according to claim 2, wherein said tip rack is a molded plastic having a plurality of tip insertion holes arranged at given intervals.

4. An analyzing apparatus according to claim 1, wherein said tip holder comprises:

a tip connecting station at which said held nozzle tip is connected to said nozzle of said pipetting device;

a sample receiving station at which a sample delivered from said connected tip is received by a reaction vessel; and a tip detaching station at which said connected nozzle tip after said sample is delivered is detached from said nozzle.

5. An analyzing apparatus according to claim 4, wherein said tip connecting station, said sample receiving station and said tip detaching station are arranged in said first given region in a straight line.

6. An analyzing apparatus according to claim 4, further comprising a bag for collecting used nozzle tips below said tip detaching station.

7. An analyzing apparatus according to claim 4, further comprising:

a tip cleaning unit in said first given region, said connected nozzle tip being cleaned with said tip cleaning unit after a reagent is transferred to said reaction vessel, after a sample is transferred to said reaction vessel after cleaning, and after being detached from said nozzle at said tip detaching station.

8. An analyzing apparatus according to claim 1, further comprising:

a reagent positioning device having a turntable on which reagent containers are arranged along each of plural concentric circles; and a sample supplying device for supplying a sample cup to a sample sucking position;

wherein said nozzle of said pipetting device is moved so as to cross said plural concentric circles off the rotating center of said turntable of said reagent positioning device, and linearly moved above said tip holder, said reagent positioning device, and said sample supplying device.

9. An analyzing apparatus according to claim 8, further comprising:

a vessel rack on which a plurality of unused reaction vessels are arranged; and an incubator unit for keeping a reaction vessel receiving a sample and a reagent at a given temperature so as to incubate a mixture thereof;

wherein said transfer device transfers a reaction vessel from said vessel rack to said tip holder using said gripper, and transfers a reaction vessel containing a sample and a reagent from said tip holder to said incubator unit using said gripper.

10. An analyzing apparatus according to claim 9, further comprising introducing means for introducing an incubated reaction solution from a reaction vessel placed at a reaction solution sucking position to a measuring device, said transfer device transferring said reaction vessel containing said incubated reaction solution from said incubator unit to said reaction solution sucking position using said gripper.

11. An analyzing apparatus according to claim 1, wherein said tip holder is installed in a region overlapped by said first and second given regions.

12. An analyzing apparatus according to claim 1, wherein said tip holder includes a tip connecting station to which said transfer device delivers and releases said nozzle tip, and at which said pipetting device connects said nozzle to said nozzle tip.

13. An analyzing apparatus according to claim 12, wherein said tip connecting station accommodates only one nozzle tip at a time for said connection of said nozzle to said nozzle tip by said pipetting device.

* * * * *